(12) United States Patent
Ryu (10) Patent No.: US 11,951,309 B2
(45) Date of Patent: Apr. 9, 2024

(54) METHOD, APPARATUS, AND PROGRAM FOR CONTROLLING STIMULATOR LINKED WITH IMAGE DATA

(71) Applicant: Samsung Life Public Welfare Foundation, Seoul (KR)

(72) Inventor: Gyu Ha Ryu, Seoul (KR)

(73) Assignee: Samsung Life Public Welfare Foundation, Seoul (KR)

(*) Notice: Subject to any disclaimer, the term of this patent is extended or adjusted under 35 U.S.C. 154(b) by 839 days.

(21) Appl. No.: 17/049,379

(22) PCT Filed: Apr. 22, 2019

(86) PCT No.: PCT/KR2019/004813
§ 371 (c)(1),
(2) Date: Oct. 21, 2020

(87) PCT Pub. No.: WO2019/208987
PCT Pub. Date: Oct. 31, 2019

(65) Prior Publication Data
US 2021/0249114 A1 Aug. 12, 2021

(30) Foreign Application Priority Data
Apr. 23, 2018 (KR) .................. 10-2018-0046987

(51) Int. Cl.
*G16H 20/30* (2018.01)
*A61B 5/00* (2006.01)
(Continued)

(52) U.S. Cl.
CPC ........ *A61N 1/36025* (2013.01); *A61B 5/0036* (2018.08); *G16H 20/30* (2018.01);
(Continued)

(58) Field of Classification Search
CPC ............ A61N 1/36025; A61N 1/36031; A61N 1/3603; A61N 2/006; A61N 5/0622;
(Continued)

(56) References Cited

U.S. PATENT DOCUMENTS

2007/0043268 A1 2/2007 Russell
2012/0157752 A1* 6/2012 Nishikawa ............. A61N 2/008
600/15
(Continued)

FOREIGN PATENT DOCUMENTS

JP 2014-133133 A 7/2014
KR 10-2009-0054887 A 6/2009
(Continued)

OTHER PUBLICATIONS

Extended European Search Report prepared for corresponding European Application 19791780.0 dated Dec. 21, 2021.
(Continued)

*Primary Examiner* — Ankit D Tejani
*Assistant Examiner* — Joshua Brendon Solomon
(74) *Attorney, Agent, or Firm* — McCarter & English, LLP (57) ABSTRACT

A method of controlling a stimulator by using image data includes receiving coordinate data of a plurality of stimulus units from a user terminal or a stimulator connected to the user terminal, obtaining, from a hospital terminal, primary image data including coordinate data of a target area estimated to be an affected area of a user, generating matching data by matching the coordinate data of the plurality of stimulus units to the primary image data, generating stimulus intensity control data capable of controlling stimulus intensities of the plurality of stimulus units by using the matching data, and transmitting the stimulus intensity control data to the user terminal.

9 Claims, 10 Drawing Sheets

(51) Int. Cl.
*A61N 1/36* (2006.01)
*G16H 40/63* (2018.01)
*A61B 5/055* (2006.01)

(52) U.S. Cl.
CPC .............. *G16H 40/63* (2018.01); *A61B 5/055* (2013.01); *A61N 1/36031* (2017.08)

(58) Field of Classification Search
CPC ...... A61B 5/0036; A61B 5/055; G16H 20/30; G16H 20/40; G16H 40/63; G16H 40/60; G16H 30/40; G16H 30/20
See application file for complete search history.

(56) References Cited

U.S. PATENT DOCUMENTS

2014/0194722 A1  7/2014  Lee et al.
2017/0177827 A1  6/2017  Achatz et al.

FOREIGN PATENT DOCUMENTS

| | | |
|---|---|---|
| KR | 10-2015-0134139 A | 12/2015 |
| KR | 10-2017-0027274 A | 3/2017 |
| KR | 10-1778063 B1 | 9/2017 |
| WO | WO 2008/066316 A1 | 6/2008 |
| WO | WO 2015/178680 A1 | 11/2015 |
| WO | WO 2018/070712 A2 | 4/2018 |

OTHER PUBLICATIONS

International Search Report (including English translation of ISR) and Written Opinion prepared by Korean Intellectual Property Office, acting as the International Searching Authority, for international application PCT/KR2019/004813 dated Jul. 24, 2019.

* cited by examiner

METHOD, APPARATUS, AND PROGRAM FOR CONTROLLING STIMULATOR LINKED WITH IMAGE DATA

CROSS-REFERENCE TO RELATED APPLICATIONS

This application is the National Stage entry under 35 U.S.C. § 371 of International Application Number PCT/KR2019/004813 filed on Apr. 22, 2019, published on Oct. 31, 2019 under publication number WO 2019/208987 A1, which claims the benefit of priority under 35 U.S.C. § 119 of Korean patent application number 10-2018-0046987 filed Apr. 23, 2018.

TECHNICAL FIELD

The present disclosure relates to a method, apparatus, and program for controlling a stimulator by using image data.

BACKGROUND ART

With the rapid development of the healthcare industry, stimulators with various purposes have emerged. A stimulator treats a user or relieves symptoms by applying various stimuli such as electric current, a magnetic field, light, ultrasound, and vibrations, inside or outside the user's body.

In recent years, a stimulator that may control an operation through an application in conjunction with a smartphone has appeared.

DESCRIPTION OF EMBODIMENTS

Technical Problem

Existing stimulators have various modes to allow users to choose a stimulus method they prefer. However, because these stimulator modes operate according to a predetermined algorithm, there is a problem in that user-customized stimulus may not be applied and, in severe cases, the user's symptoms worsen.

However, this objective is only an example, and the scope of the present disclosure is not limited thereby.

Technical Solution to Problem

According to an aspect of the present disclosure, a method of controlling a stimulator by using image data includes receiving coordinate data of a plurality of stimulus units from a user terminal or a stimulator connected to the user terminal, obtaining, from a hospital terminal, primary image data including coordinate data of a target area estimated to be an affected area of a user, generating matching data by matching the coordinate data of the plurality of stimulus units to the primary image data, generating stimulus intensity control data capable of controlling stimulus intensities of the plurality of stimulus units by using the matching data, and transmitting the stimulus intensity control data to the user terminal.

Advantageous Effects of Disclosure

According to a method of controlling a stimulator by using image data, according to an embodiment of the present disclosure, customized stimulus intensity control data suitable for a user's symptoms may be generated because stimulus intensity is controlled based on image data such as the user's magnetic resonance imaging (MRI) data obtained by imaging in a hospital.

In addition, by matching stimulus unit coordinate data to the image data, stimulus intensity control data suitable for the user's body shape may be generated.

In addition, by aggregating the user's image data records obtained by imaging in a hospital, stimulus intensity control data suitable for the user's prognosis may be generated. Accordingly, the therapeutic effect on the user using the stimulator may be increased.

Obviously, the scope of the present disclosure is not limited by these effects.

BEST MODE

A method of controlling a stimulator by using image data, according to an embodiment of the present disclosure includes receiving coordinate data of a plurality of stimulus units from a user terminal or a stimulator connected to the user terminal, obtaining, from a hospital terminal, primary image data including coordinate data of a target area estimated to be an affected area of a user, generating matching data by matching the coordinate data (hereinafter, referred to as stimulus unit coordinate data) of the plurality of stimulus units to the primary image data, generating stimulus intensity control data capable of controlling stimulus intensities of the plurality of stimulus units by using the matching data, and transmitting the stimulus intensity control data to the user terminal.

The generating of the matching data may include matching the stimulus unit coordinate data to the primary image data such that a curved surface formed by the stimulus unit coordinate data comes into contact with the user's body surface indicated in the primary image data.

The generating of the stimulus intensity control data may include setting a stimulus intensity of a stimulus unit within a specific distance from the target area from among the plurality of stimulus units to be different from a stimulus intensity of a stimulus unit outside the specific distance from the target area.

The method may further include: after the transmitting of the stimulus intensity control data, receiving secondary image data from the hospital terminal, and comparing the primary image data with the secondary image data to regenerate stimulus intensity control data capable of controlling the stimulus intensities of the plurality of stimulus units.

An apparatus for controlling a stimulator by using image data, according to an embodiment of the present disclosure includes a receiver configured to receive coordinate data of a plurality of stimulus units from a user terminal or a stimulator connected to the user terminal, an image data obtainer configured to obtain, from a hospital terminal, primary image data including coordinate data of a target area, a matching data generator configured to generate matching data by matching the coordinate data of the plurality of stimulus units to the primary image data, a stimulus intensity control data generator configured to generate stimulus intensity control data capable of controlling stimulus intensities of the plurality of stimulus units by using the matching data, and a transmitter configured to transmit the stimulus intensity control data to the user terminal.

An embodiment of the present disclosure provides a computer program stored in a medium to execute the method by using a computer.

Other aspects, features, and advantages other than those described above will be apparent from the following drawings, claims, and detailed description of the present disclosure.

MODE OF DISCLOSURE

Since the present disclosure may have various modifications and several embodiments, embodiments are shown in the drawings and will be described in detail. Effects, features, and a method of achieving the same will be specified with reference to the embodiments described below in detail together with the attached drawings. However, the embodiments may have different forms and should not be construed as being limited to the descriptions set forth herein.

It will be understood that although the terms "first", "second", etc. may be used herein to describe various components, these components should not be limited by these terms and are only used to distinguish one component from another.

As used herein, the singular forms "a", "an" and "the" are intended to include the plural forms as well, unless the context clearly indicates otherwise.

It will be further understood that the terms "includes", "including", "has" and/or "having" used herein specify the presence of stated features or components, but do not preclude the presence or addition of one or more other features or components.

It will be understood that when a layer, region, or component is referred to as being "formed on," another layer, region, or component, it may be directly or indirectly formed on the other layer, region, or component. That is, for example, intervening layers, regions, or components may be present.

When a certain embodiment may be implemented differently, a specific process order may be performed differently from the described order. For example, two consecutively described processes may be performed substantially at the same time or performed in an order opposite to the described order.

Sizes of elements in the drawings may be exaggerated or reduced for convenience of description. In other words, since sizes and thicknesses of components in the drawings are arbitrarily illustrated for convenience of description, the following embodiments are not limited thereto.

In the present specification, 'image data' refers to data obtained by imaging a user's body, and may include, for example, computerized tomography (CT) image data, magnetic resonance imaging (MRI) image data, positron emission tomography (PET) image data, ultrasound image data, and/or the like. Hereinafter, an example in which 'image data' is 'MRI image data' will be mainly described. However, the present disclosure is not limited thereto.

In the present specification, 'stimulator S' refers to a device that applies a stimulus to a user inside or outside the user's body. The stimulator S may be a device that applies stimulus to a user in a manner such as electric current, electric field, magnetic field, light, ultrasound, or vibration. Hereinafter, an example in which the stimulator S includes an electrode attached to a user's head to apply electrical stimulus thereto will be mainly described. However, the present disclosure is not limited thereto. For example, the stimulator S may be worn on a user's head and may give electrical stimulus to the user's brain.

In the present specification, 'user terminal UT' is a device that is used by a user and may communicate with the outside, and may be, for example, a mobile phone. However, the present disclosure is not limited thereto.

In the present specification, 'hospital terminal HT' is a device that is used by medical staff in a hospital and may communicate with the outside, and may be, for example, a mobile phone, a mobile tablet, a computer, or a hospital medical record storage server. However, the present disclosure is not limited thereto.

In the present specification, 'target area' is a user's affected area or an area estimated to be the affected area in image data, and may refer to a body area that requires treatment or symptom relief using the stimulator S. For example, the target area may refer to an area where stricture of blood vessels, occlusion, aneurysm bleeding, etc. occurs, a lesion area, or an ischemic area (i.e., a penumbra area) where a stroke occurs. However, the present disclosure is not limited thereto.

Figure 1:
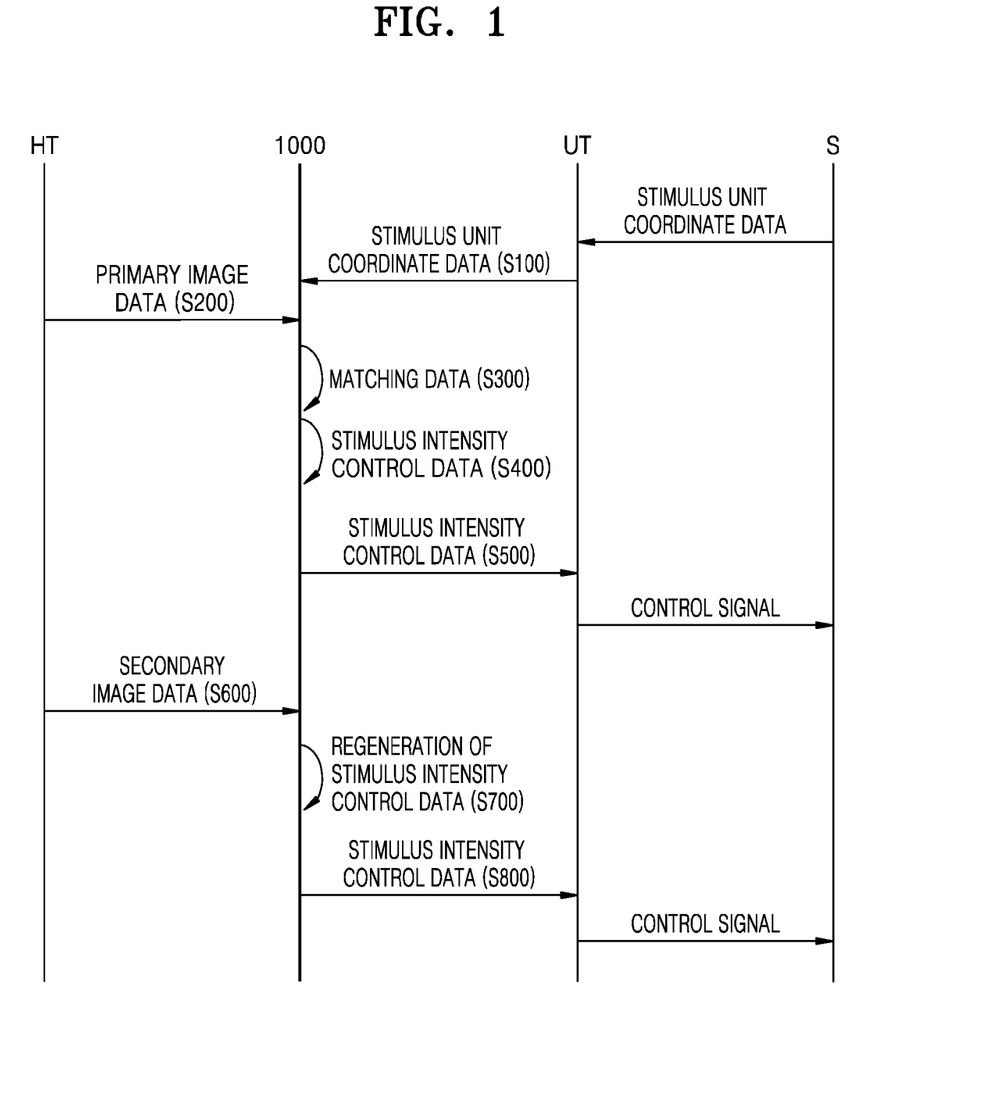
FIG. 1 is a data flow diagram of a method of controlling a stimulator by using image data, according to an embodiment of the present disclosure.

FIG. 1 is a data flow diagram of a method of controlling a stimulator by using image data, according to an embodiment of the present disclosure.

The method of controlling a stimulator by using image data, according to the embodiment of the present disclosure, includes receiving stimulus unit coordinate data (operation S100), obtaining primary image data (operation S200), generating matching data (operation S300), generating stimulus intensity control data (operation S400), and transmitting the stimulus intensity control data to a user terminal UT (operation S500). Each of the operations may be performed by a control device 1000. The control device 1000 will be described later with reference to FIG. 10.

Referring to FIG. 1, first, operation S100 of receiving coordinate data of a plurality of stimulus units from the user terminal UT or a stimulator S is performed.

In the present disclosure, it is assumed that the stimulator S is a device capable of applying stimulus to various body parts of a user. For example, the stimulator S may include a plurality of electrodes or patches. The plurality of electrodes or patches may be attached to a user's body, for example, on the user's head, to apply stimulus to the user. On/off and intensity of the plurality of electrodes may be controlled differently.

The stimulus unit coordinate data may refer to a coordinate set of a stimulus unit included in the stimulator S. For example, the stimulus unit may be a device that applies stimulus to a user in a manner such as electric current, electric field, magnetic field, light, ultrasound, or vibration.

The stimulus unit may be, for example, an electrode. In this case, the coordinates of the stimulus unit may refer to a 'position' of each electrode. The coordinates of each stimulus unit may be appropriately defined as the center of gravity of the stimulus unit. This will be described later in the description related to FIG. 2.

The stimulator S is connected to the user terminal UT. In this case, being 'connected' may refer to a state in which the stimulator S and the user terminal UT may communicate with each other by wire and/or wirelessly. For example, the stimulator S and the user terminal UT may be connected to each other by Bluetooth, etc., and a user may control the on/off, stimulus time, stimulus intensity, and the like of the stimulator S through the user terminal UT.

The stimulator S may store information about the stimulus unit coordinate data. Thereafter, when the stimulator S and the user terminal UT are connected to each other, the stimulator S may transmit the stimulus unit coordinate data to the user terminal UT. The control device 1000 may indirectly receive stimulus unit data from the user terminal UT.

Operation S200 of obtaining primary image data including coordinate data and symptom degree data of a target area from a hospital terminal HT is performed. In FIG. 1, it is shown that operation S200 is performed after operation S100 of receiving stimulus unit coordinate data. However, the present disclosure is not limited thereto.

The control device 1000 may receive, for example, raw MRI data from the hospital terminal HT and image-process the received raw MRI data to calculate primary image data including coordinate data and symptom degree data of the target area. Alternatively, the control device 1000 may receive primary image data obtained by image processing in the hospital terminal HT.

The coordinate data of the target area may refer to a coordinate value of the target area (or an affected area) in an image. The symptom degree data may refer to the signal intensity of the target area in the image or the volume of the target area. This will be described later in the description related to FIG. 3.

Thereafter, operation S300 of generating matching data by matching the stimulus unit coordinate data received from the user terminal UT to the primary image data obtained from the hospital terminal HT is performed. The control device 1000 generates matching data by integrating data from the user terminal UT and the hospital terminal HT. This will be described later in the description related to FIG. 4.

Thereafter, operation S400 of generating stimulus intensity control data by using the matching data is performed. The stimulus intensity control data may include a stimulus intensity control signal capable of controlling the stimulus intensity of each stimulus unit of the stimulator S. In addition, the stimulus intensity control data may further include a stimulus time control signal capable of controlling the stimulus time of the stimulator S. That is, the stimulus intensity control data may include data on how to control a plurality of stimulus units included in the stimulator S differently.

Thereafter, operation S500 of transmitting, by the control device 1000, the stimulus intensity control data to the user terminal UT is performed. After the user terminal UT receives the stimulus intensity control data, the user terminal UT may transmit a control signal for controlling the stimulator S to the stimulator S based on the received stimulus intensity control data. The stimulator S operates according to a control signal based on the stimulus intensity control data generated by the control device 1000. That is, stimulus is not applied to a user according to a predetermined algorithm of the stimulator S itself, but a user-customized stimulus is applied to the user based on data obtained by analyzing image data of the user.

Figure 2:
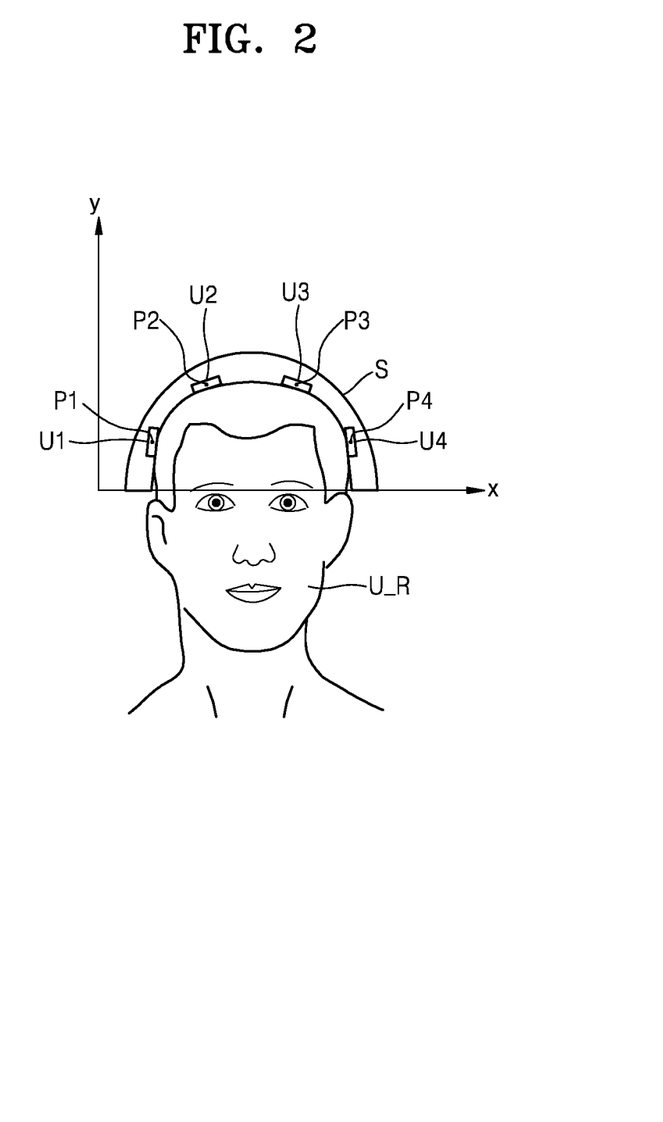
FIG. 2 is a diagram conceptually illustrating coordinate data of a plurality of stimulus units of a stimulator.

FIG. 2 is a diagram conceptually showing coordinate data of a plurality of stimulus units of a stimulator S. In FIG. 2, for convenience, a stimulator S having four stimulus units U1, U2, U3, and U4 is conceptually illustrated. However, the present disclosure is not limited thereto. For convenience of description, FIG. 2 is illustrated in two dimensions (2D).

The stimulator S may have coordinate data P1, P2, P3, and P4 of the stimulus units U1, U2, U3, and U4 according to the shape/size of the head of a standard user U_R. In this case, the coordinate data P1, P2, P3, and P4 of the stimulus units U1, U2, U3, and U4 may have a fixed value using a specific point of the stimulator S as a reference point. In this case, the coordinate data P1, P2, P3, and P4 of the stimulus units U1, U2, U3, and U4 may be defined in a stimulator coordinate system (x, y).

When the stimulator S has flexibility such that the shape thereof may be changed according to the shape/size of a user's head, when a user wears the stimulator S, actual positions of the stimulus units U1, U2, U3, and U4 may be different from the coordinate data P1, P2, P3, and P4.

Figure 3:
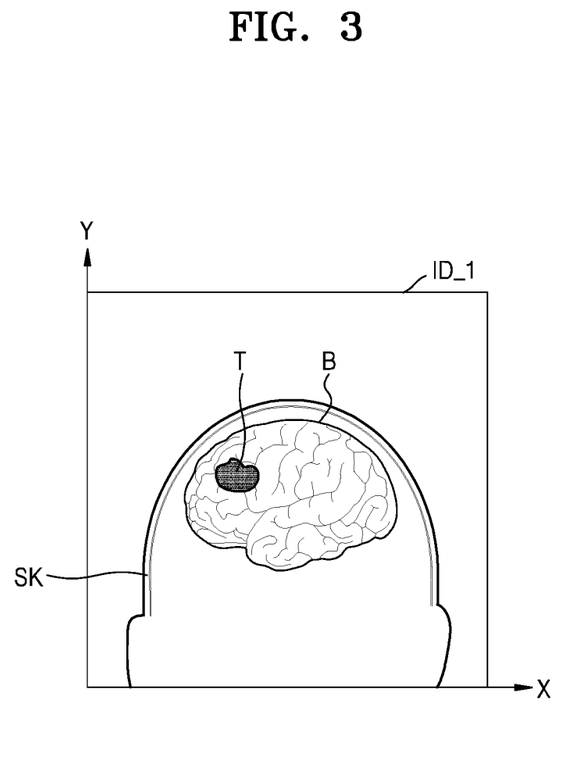
FIG. 3 is a diagram conceptually illustrating primary image data.

FIG. 3 is a diagram conceptually showing primary image data ID_1. FIG. 3 illustrates that a brain B and a skull SK are shown in primary image data ID_1 obtained by imaging a user's head.

The control device 1000 according to an embodiment may image-process MRI data and set, as a target area T, an area having a signal strength which is equal to or greater than or equal to or less than a specific value. In this case, the control device 1000 may determine a set of voxels of the target area T, which are concentrated within a specific distance range, as one area, and may obtain coordinate data of the target area T by averaging the coordinates of voxels included in the one area. In addition, symptom degree data may be obtained based on the average of signal intensity and/or the number of voxels. The coordinate data of the target area T is defined in the image coordinate system (X, Y).

Figure 4:
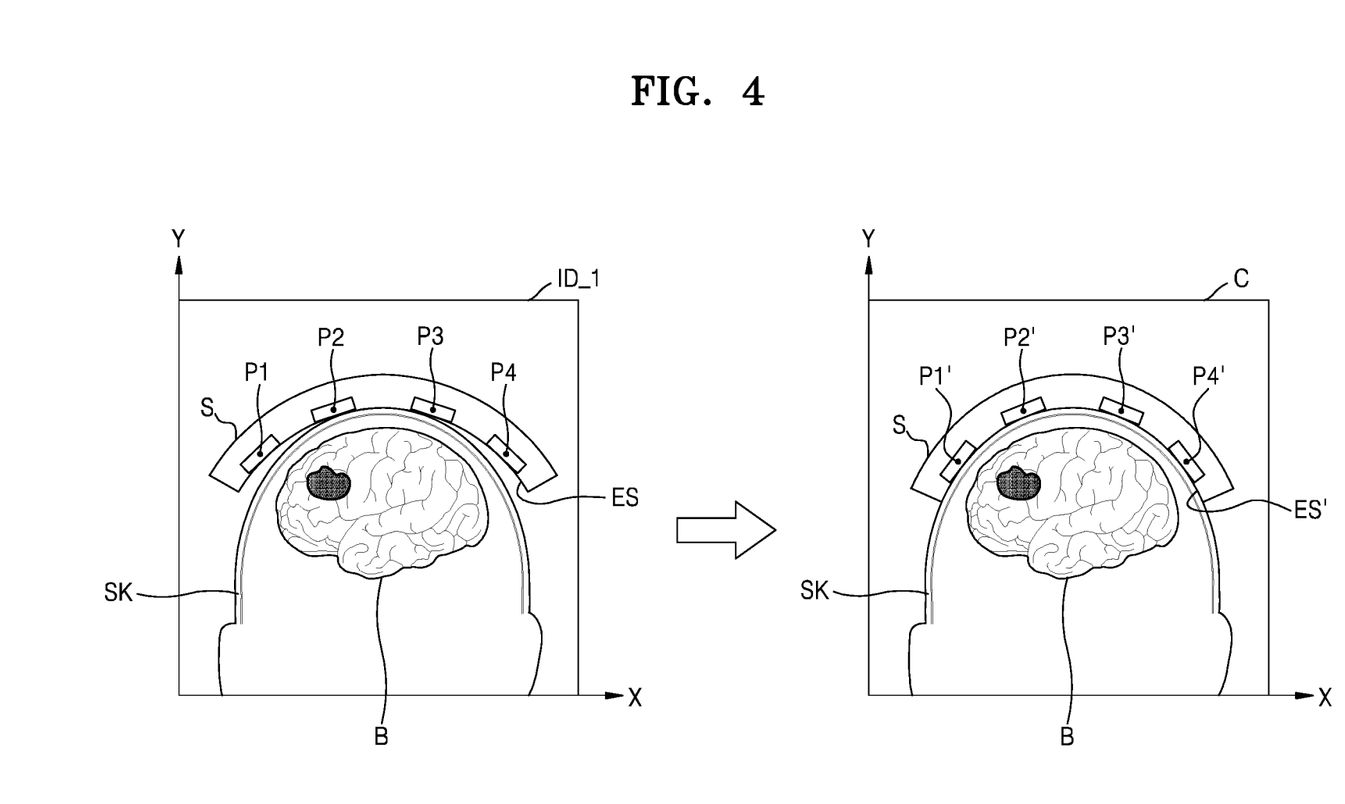
FIG. 4 is a diagram conceptually illustrating the generation of matching data by matching stimulus unit coordinate data to primary image data.
Figure 5:
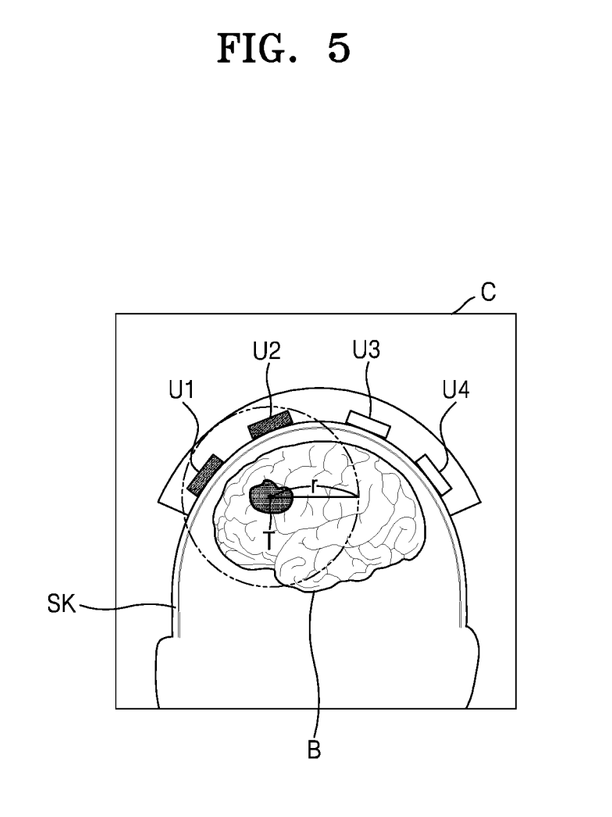
FIGS. 5 to 8 are diagrams illustrating various methods of generating stimulus intensity control data.
Figure 6:
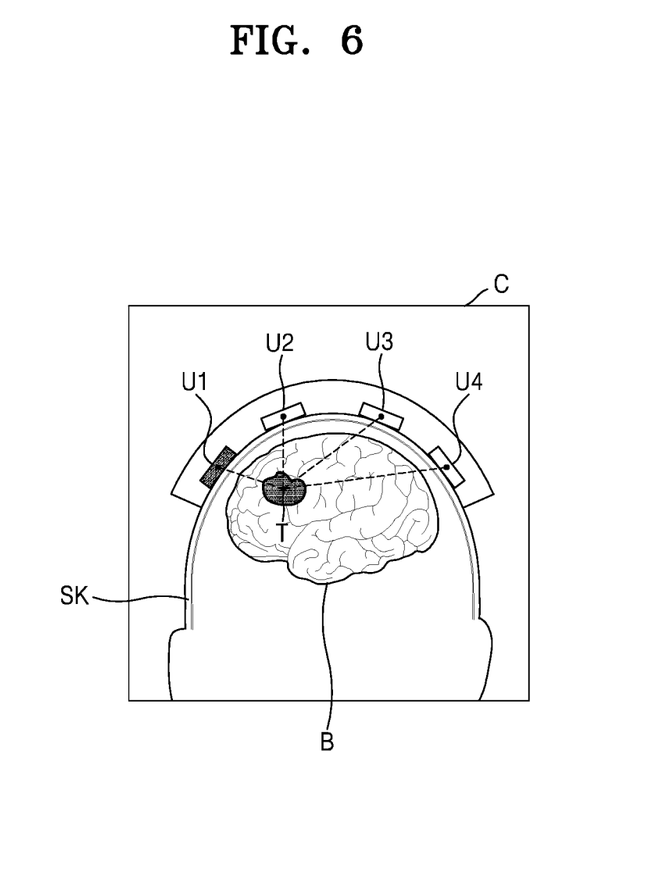

FIG. 4 is a diagram conceptually showing generating matching data C by matching stimulus unit coordinate data to primary image data.

According to an embodiment, operation S100 of generating matching data may include matching stimulus unit coordinate data to primary image data such that a curved surface ES formed by the coordinate data of the plurality of stimulus units comes into contact with a user's body surface indicated in the primary image data.

The control device 1000 matches the coordinate data (hereinafter, referred to as stimulus unit coordinate data) P1, P2, P3, and P4 received from the user terminal UT or the stimulator S to the primary image data ID_1 received from the hospital terminal HT. More specifically, the control device 1000 may change the curved surface ES formed by the stimulus unit coordinate data such that the stimulus unit coordinates P1, P2, P3, and P4 come into contact with a user's body surface shown in the primary image data ID_1.

For example, referring to the left figure of FIG. 4, because the curved surface ES formed by the stimulus unit coordinate data P1, P2, P3, and P4 is calculated based on the body (e.g., head) of the standard user U_R, the curved surface ES may not match the outer surface of the body (e.g., the outer surface of the skull) of an actual user. Accordingly, the control device 1000 may properly match the curved surface ES to the outer surface of a user's skull SK such that the curved surface ES, which is formed by the stimulus unit coordinate data P1, P2, P3, and P4 received from the stimulator S, comes into contact with the outer surface of the user's skull SK shown in the primary image data ID_1.

Referring to the right figure of FIG. 4, in the matching data C, a curved surface ES' formed by stimulus unit coordinate data P1', P2', P3', and P4' matches the outer surface of the skull SK. That is, the control device 1000 may match data received from the user terminal UT to data received from the hospital terminal HT, thereby modeling a state in which a user wears the stimulator S.

FIGS. 5 to 8 are diagrams showing various methods of generating stimulus intensity control data.

According to an embodiment, operation S400 of generating stimulus intensity control data may include setting the stimulus intensity of a stimulus unit within a specific distance from a target area from among a plurality of stimulus units to be different from the stimulus intensity of a stimulus unit outside the specific distance from the target area.

In an embodiment, the control device 1000 may set the stimulus intensity of a stimulus unit within a specific distance from the target area to be greater than the stimulus intensity of a stimulus unit outside the specific distance from the target area. For example, referring to FIG. 5, the control device 1000 may generate stimulus intensity control data to turn on only the stimulus units U1 and U2 within a specific distance r from the target area T and turn off the remaining stimulus units U3 and U4. In this case, the stimulus intensity in the stimulus unit U1 and the stimulus intensity in the stimulus unit U2 may be set to be in inverse proportion to the distance to the target area T.

In an embodiment, the control device 1000 may calculate distances between a target area and a plurality of stimulus units (or electrodes) and generate stimulus intensity control data such that the stimulus intensity of a stimulus unit closest to the target area is greater than that of other stimulus units. For example, referring to FIG. 6, the control device 1000 may generate stimulus intensity control data to turn on only the stimulus unit U1 closest to the target area T and turn off the remaining stimulus units U2, U3, and U4. Alternatively, the control device 1000 may generate stimulus intensity control data to turn on a specific number of stimulus units in an order of close distance from the target area T.

Figure 7:
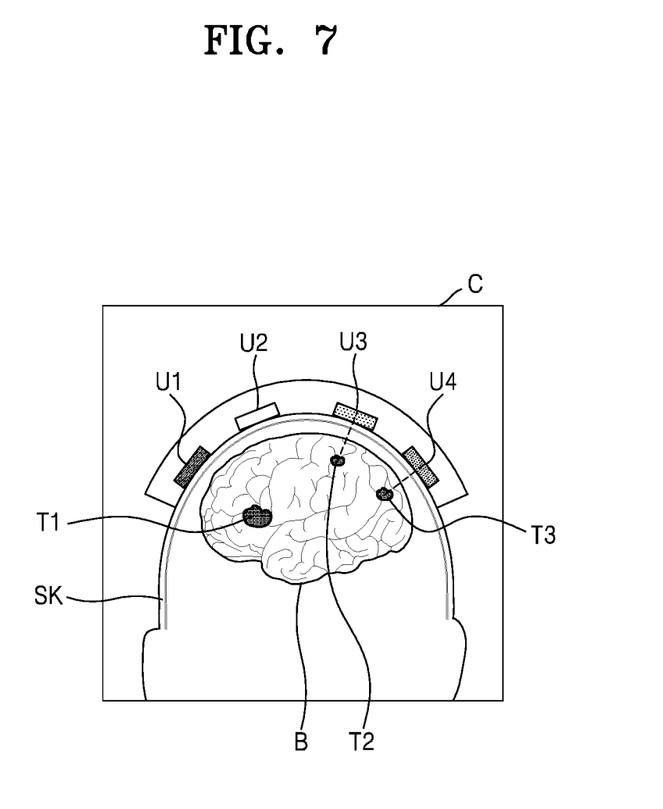

When there are a plurality of target areas, the control device 1000 may generate stimulus intensity control data such that the nearest stimulus unit is turned on for each of the target areas. For example, as shown in FIG. 7, when there are three target areas T1, T2, and T3, the control device 1000 may generate stimulus intensity control data to turn on stimulus units U1, U3, and U4 respectively closest to the target areas T1, T2, and T3.

The stimulus intensity may be a function of the volume of a target area. For example, as the volume of the target area increases, the stimulus intensity may also increase. Furthermore, the stimulus intensity may be a function of the degree of symptoms of a target area. For example, as the signal intensity of the target area increases, the stimulus intensity may also increase.

According to an embodiment, operation S400 of generating stimulus intensity control data may include an operation of projecting a target area on a user's body surface indicated in the primary image data and setting stimulus intensity control data to turn on a stimulus unit closest to a projected target area. For example, referring to FIG. 8, the control device 1000 may project two target areas T1 and T2 on the surface of a user's skull in a y-axis direction and generate stimulus intensity control data to turn on stimulus units U2 and U3 respectively closest to projected areas P T1 and P T2.

Figure 8:
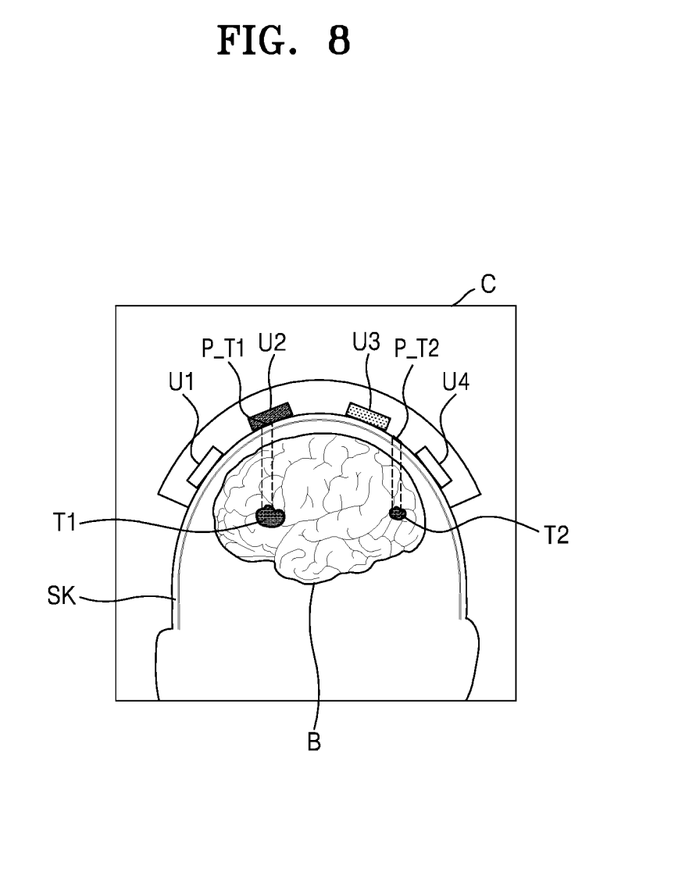

The control device 1000 transmits stimulus intensity control data generated according to the above-described embodiment to the user terminal UT. After receiving the stimulus intensity control data, the user terminal UT may generate a control signal for setting stimulus time, stimulus intensity, etc. according to a user's input and the like and operate the stimulator S by wire or wirelessly. As a result, a signal for controlling the stimulator S is generated in conjunction with the image data by the control device 1000.

The stimulus intensity control data includes a stimulus area control signal capable of controlling a stimulus area of the stimulator S and a stimulus intensity control signal capable of controlling the stimulus intensity of the stimulator S. In addition, the stimulus intensity control data may further include a stimulus time control signal capable of controlling the stimulus time of the stimulator S. The control device 1000 generates user-customized stimulus intensity control data after determining the coordinates of a target area from matching data. That is, the stimulus intensity control data includes control data on the relative strengths of a plurality of electrodes included in the stimulator S.

Thereafter, the control device 1000 transmits the stimulus intensity control data to the user terminal UT. After receiving the stimulus intensity control data, the user terminal UT may transmit a control signal for controlling the stimulator S to the stimulator S. In this case, a user may control the overall operating time and overall intensity of the stimulate S. The stimulator S operates according to a control signal based on the stimulus intensity control data generated by the control device 1000. In other words, stimulus is not applied to a user according to a predetermined algorithm of the stimulator S itself, but a stimulus is applied to the user based on data obtained by analyzing image data such as MRI data of the user.

The method of controlling a stimulator by using image data, according to the embodiment may further include, after operation S500, receiving secondary image data from the hospital terminal HT (operation S600) and comparing the primary image data with the secondary image data to regenerate stimulus intensity control data capable of controlling stimulus intensities of the plurality of stimulus units (operation S700).

Referring back to FIG. 1, after operation S500, operation S600 of receiving secondary image data is performed.

After several days or months have passed after operation S500, the user may revisit the hospital and take an image such as an MRI image again. In the present specification, after the primary image data is obtained, image data obtained by imaging in the same format will be referred to as secondary image data. The control device 1000 may receive, for example, raw MRI data from the hospital terminal HT and image-process the received raw MRI data to calculate secondary image data including coordinate data and symptom degree data of a target area. Alternatively, the control device 1000 may receive secondary image data obtained by image processing in the hospital terminal HT.

Thereafter, after comparing or matching the primary image data to the secondary image data, operation S700 of regenerating stimulus intensity control data by using matching data is performed.

Figure 9:
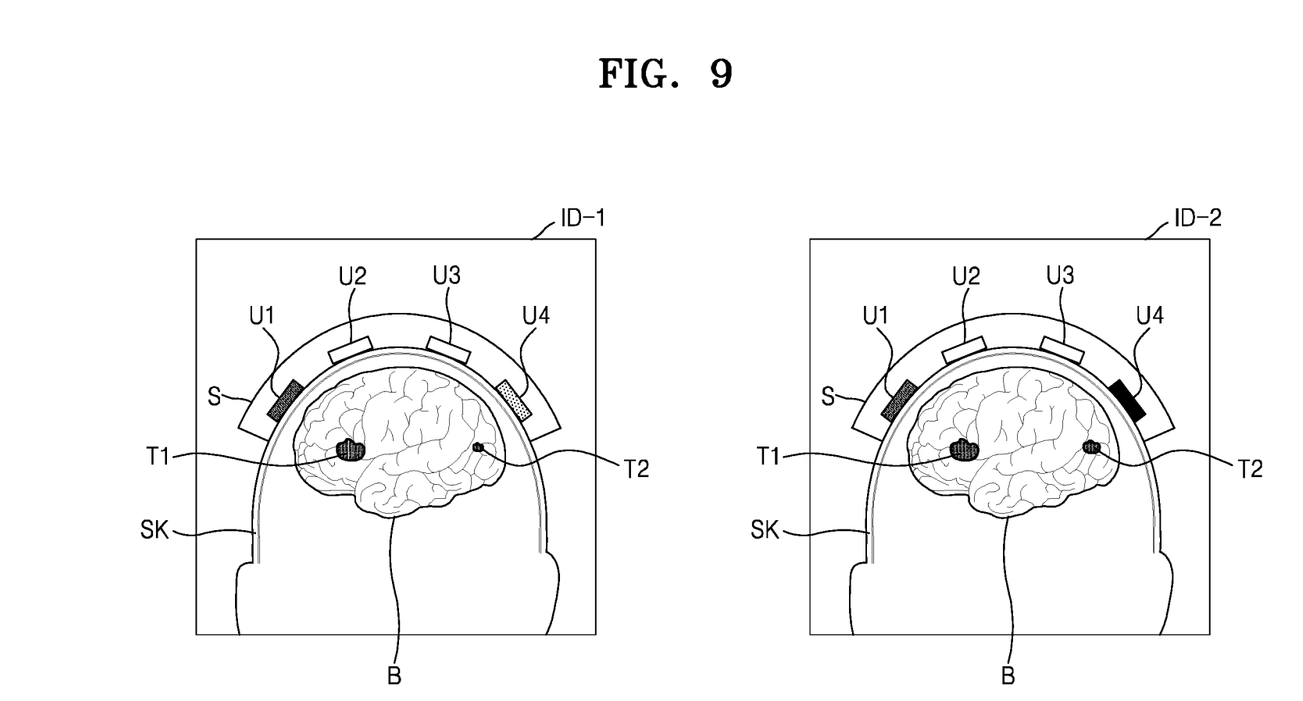
FIG. 9 is a diagram conceptually illustrating examples of primary image data and secondary image data.

FIG. 9 is a diagram conceptually showing examples of primary image data ID_1 and secondary image data ID_2.

The primary image data ID_1 and the secondary image data ID_2 may be image data captured with respect to the same user at intervals of days or months. The control device 1000 may match the primary image data ID_1 to the secondary image data ID_2 and compare the difference between the two image data On the left side of FIG. 9, the primary image data ID_1 in which two target areas, that is, a first target area T1 and a second target area T2, are displayed is illustrated. In this case, the volume of the first target area T1 is greater than the volume of the second target area T2. In this case, the control device 1000 may generate, in operation S400 of generating stimulus intensity control data, stimulus intensity control data such that the stimulus intensity of a first stimulus unit U1 closest to the first target area T1 is greater than that of a fourth stimulus unit U4 closest to the second target area T2, and may transmit the generated stimulus intensity control data to the user terminal UT (operation S500). The user terminal UT operates the stimulator S based on the stimulus intensity control data. In this case, a user receives stimulus in a state in which the stimulus intensity of the first stimulus unit U1 is greater than that of the fourth stimulus unit U4.

Thereafter, when the user visits the hospital again and takes an MRI image again, the hospital terminal HT may transmit the secondary image data ID_2 to the control device 1000. When the control device 1000 compares the secondary image data ID_2 with the primary image data ID_1, the control device 1000 may determine that the volume of the first target area T1 in the secondary image data ID_2 has remained the same and the volume of the second target area T2 in the secondary image data ID_2 has been increased. In this case, although the volume of the second target area T2 is less than the volume of the first target area T1, the second target area T2 may be more dangerous than the first target area T1 because the volume of the second target area T2 is increasing. In this case, the control device 1000 may regenerate stimulus intensity control data to further increase the stimulus intensity of the stimulus unit U4 close to the second target area T2 in order to intensively treat the second target area T2. That is, the stimulus intensity may be a function of not only the volume of a target area but also the amount of change in volume.

That is, in operation S700, the control device 1000 may match the primary image data ID_1 to the secondary image data ID_2 and then select a target area whose volume is increasing, based on a difference between image signals, and then may regenerate stimulus intensity control data for applying a larger stimulus to a stimulus unit close to the selected target area and transmit the regenerated stimulus intensity control data to the user terminal UT. Thereafter, the user terminal UT may operate the stimulator S based on the regenerated stimulus intensity control data.

That is, the control device 1000 may aggregate a user's image data records obtained by imaging in a hospital, generate stimulus intensity control data suitable for the user's prognosis, and transmit the stimulus intensity control data to the user terminal UT. The user terminal UT may transmit a control signal to the stimulator S based on stimulus intensity control data suitable for the user's prognostic characteristics.

Although not shown in the drawings, after the control signal is transmitted to the stimulator S and the stimulator S operates, the control device 1000 may receive user feedback data from the user terminal UT. For example, after the use of the stimulator S is completed, a user may input satisfaction information about the degree of pain relief by the stimulator S into the user terminal UD. In addition, the control device 1000 may receive, from the user terminal UT, stimulator operation record data regarding when the stimulator S was operated and/or how long the stimulator S has been operated. The control device 1000 may transmit the user's feedback data and/or the stimulator operation record data to the hospital terminal HT. Medical staff using the hospital terminal HT may monitor data received from the control device 100 and transmit a message appropriate to the situation to the user terminal UT via the control device 1000.

Figure 10:
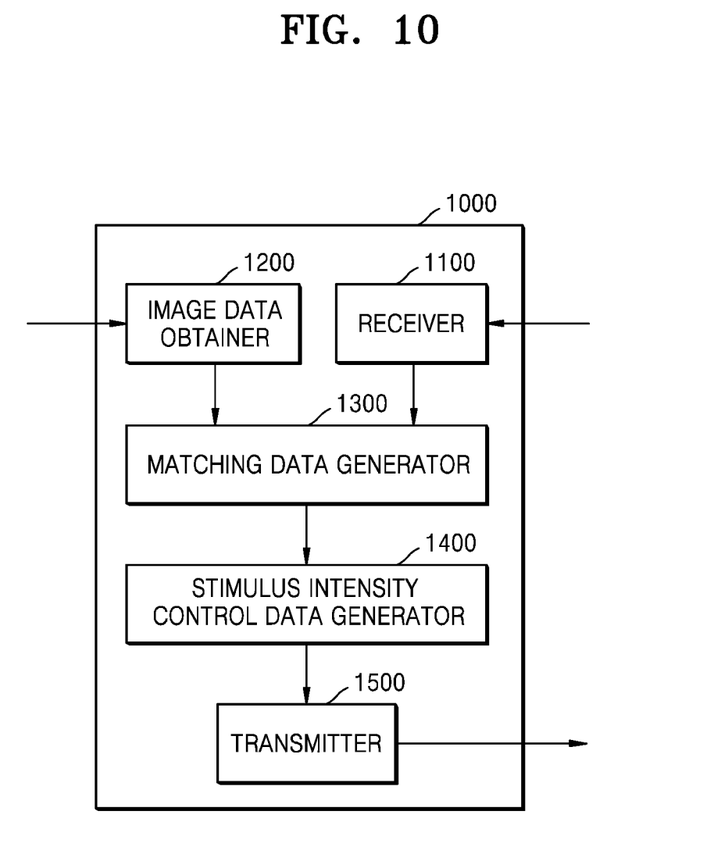
FIG. 10 is a block diagram of an apparatus for controlling a stimulator by using image data, according to an embodiment of the present disclosure.

FIG. 10 is a block diagram of an apparatus 1000 for controlling a stimulator by using image data, according to an embodiment of the present disclosure.

The apparatus 1000 (hereinafter, refer to a control device 1000) in FIG. 10 shows only components related to the present embodiment in order to prevent blurring of the features of the present embodiment. Accordingly, it may be understood by those of ordinary skill in the art related to the present embodiment that other general-purpose components may be further included in the control device 1000 in addition to the components shown in FIG. 1.

The control device 1000 according to the present embodiment may correspond to at least one processor, or may include at least one processor. Accordingly, the control device 1000 may be driven in a form included in another hardware device such as a microprocessor or a general-purpose computer system.

The inventive concept of the present disclosure may be represented by functional block configurations and various processing steps. The functional blocks may be implemented with various numbers of hardware or/and software configurations that perform specific functions. For example, the inventive concept of the present disclosure may employ integrated circuit components such as memory, processor, logic, and look-up table, which are capable of executing various functions under the control of one or more microprocessors or other control devices. Similar to how the components of the inventive concept of the present disclosure may be implemented with software programming or software elements, the inventive concept of the present disclosure may be implemented with a programming or scripting language such as C, C++, Java, or assembler by using various algorithms implemented with a combination of data structures, processes, routines, or other programming configurations. Functional aspects may be implemented with an algorithm running on one or more processors. In addition, the inventive concept of the present disclosure may employ conventional techniques for electronic environment creation, signal processing, and/or data processing. Terms such as "mechanism", "element", "means", and "configuration" may be widely used, and components of the inventive concept of the present disclosure are not limited to mechanical and physical configurations. The terms may include a meaning of a series of routines of software in connection with a processor or the like.

Referring to FIG. 10, the control device 1000 includes a receiver 1100, an image data obtainer 1200, a matching data generator 1300, a stimulus intensity control data generator 1400, and a transmitter 1500.

The receiver 1100 receives coordinate data of a plurality of stimulus units from the user terminal UT or the stimulator S connected to the user terminal UT. The receiver 1100 may receive a message related to medical information/prognosis information/symptom information from the user terminal UT and the hospital terminal HT.

The image data obtainer 1200 obtains primary image data including coordinate data of a target area from the hospital terminal HT. The image data obtainer 1200 may obtain secondary image data, tertiary image data, . . . , n-th image data in addition to the primary image data.

The matching data generator 1300 generates matching data by matching stimulus unit coordinate data to the primary image data.

The stimulus intensity control data generator 1400 generates stimulus intensity control data capable of controlling the stimulus intensities of the plurality of stimulus units by using the matching data.

According to an embodiment, the matching data generator 1300 may match the stimulus unit coordinate data to the primary image data such that a plurality of stimulus units come into contact with a user's body surface indicated in the primary image data.

According to an embodiment, the stimulus intensity control data generator 1400 may set the stimulus intensity of a stimulus unit within a specific distance from a target area from among the plurality of stimulus units to be different from the stimulus intensity of a stimulus unit outside the specific distance from the target area.

According to an embodiment, the image data obtainer 1200 may receive secondary image data from the hospital terminal HT.

According to an embodiment, the stimulus intensity control data generator 1400 may compare the primary image data with the secondary image data to regenerate stimulus intensity control data capable of controlling the stimulus intensities of the plurality of stimulus units.

The method of controlling a stimulator by using image data, according to the embodiment of the present disclosure, which has been described with reference to FIGS. 1 to 10, may be written as computer programs and may be implemented in general-use digital computers that execute the programs using a computer readable recording medium. Examples of the computer readable recording medium include magnetic storage media (e.g., ROM, floppy disks, hard disks, etc.), optical recording media (e.g., CD-ROMs, or DVDs), etc.

While the inventive concept of the present disclosure has been particularly shown and described with reference to exemplary embodiments thereof, it will be understood by those of ordinary skill in the art that various changes in form and details may be made therein without departing from the spirit and scope of the inventive concept as defined by the following claims. Therefore, the technical protection scope of the inventive concept of the present disclosure should be determined by the technical spirit of the appended claims.

INDUSTRIAL APPLICABILITY

According to one or more embodiments of the present disclosure, a method, an apparatus, and a program for controlling a stimulator by using image data are provided. In addition, the embodiments of the present disclosure may be applied to the field of health care using stimulus control technology used in industry.

The invention claimed is:

1. A method of controlling a stimulator by using image data, the method comprising:
   receiving coordinate data of a plurality of stimulus units from a user terminal or a stimulator connected to the user terminal;
   obtaining, from a hospital terminal, primary image data including coordinate data of a target area estimated to be an affected area of a user;
   generating matching data by matching the coordinate data (hereinafter, referred to as stimulus unit coordinate data) of the plurality of stimulus units to the primary image data;
   generating stimulus intensity control data capable of controlling stimulus intensities of the plurality of stimulus units by using the matching data; and
   transmitting the stimulus intensity control data to the user terminal,
   wherein the generating of the stimulus intensity control data includes setting a stimulus intensity of a stimulus unit within a specific distance from the target area from among the plurality of stimulus units to be different from a stimulus intensity of a stimulus unit outside the specific distance from the target area.

2. The method of claim 1, wherein the generating of the matching data includes matching the stimulus unit coordinate data to the primary image data such that a curved surface formed by the stimulus unit coordinate data comes into contact with the user's body surface indicated in the primary image data.

3. The method of claim 1, further comprising:
   after the transmitting of the stimulus intensity control data,
   receiving secondary image data from the hospital terminal; and
   comparing the primary image data with the secondary image data to regenerate stimulus intensity control data capable of controlling the stimulus intensities of the plurality of stimulus units.

4. An apparatus for controlling a stimulator by using image data, the apparatus comprising:
   a receiver configured to receive coordinate data of a plurality of stimulus units from a user terminal or a stimulator connected to the user terminal;
   an image data obtainer configured to obtain, from a hospital terminal, primary image data including coordinate data of a target area;
   a matching data generator configured to generate matching data by matching the coordinate data (hereinafter, referred to as stimulus unit coordinate data) of the plurality of stimulus units to the primary image data;
   a stimulus intensity control data generator configured to generate stimulus intensity control data capable of controlling stimulus intensities of the plurality of stimulus units by using the matching data; and
   a transmitter configured to transmit the stimulus intensity control data to the user terminal,
   wherein the stimulus intensity control data generator is configured to set a stimulus intensity of a stimulus unit within a specific distance from the target area from among the plurality of stimulus units to be different from a stimulus intensity of a stimulus unit outside the specific distance from the target area.

5. The apparatus of claim 4, wherein the matching data generator is configured to match the stimulus unit coordinate data to the primary image data such that the plurality of stimulus units come into contact with the user's body surface indicated in the primary image data.

6. The apparatus of claim 4, wherein the image data obtainer is configured to
   receive secondary image data from the hospital terminal, and
   the stimulus intensity control data generator is configured to compare the primary image data with the secondary image data to regenerate stimulus intensity control data capable of controlling the stimulus intensities of the plurality of stimulus units.

7. A computer program stored in a medium to execute the method of claim 1 by using a computer.

8. A computer program stored in a medium to execute the method of claim 2 by using a computer.

9. A computer program stored in a medium to execute the method of claim 3 by using a computer.

* * * * *